(12) United States Patent
Gartner et al.

(10) Patent No.: US 11,452,822 B2
(45) Date of Patent: Sep. 27, 2022

(54) RETRACTABLE SLEEVE FOR PEN NEEDLE ASSEMBLY

(71) Applicant: Embecta Corp., Andover, MA (US)

(72) Inventors: Jeremy Gartner, Wyckoff, NJ (US); Maryann S. Fam, Secaucus, NJ (US); Peter A. Girgis, East Brunswick, NJ (US)

(73) Assignee: Embecta Corp., Andover, MA (US)

( * ) Notice: Subject to any disclaimer, the term of this patent is extended or adjusted under 35 U.S.C. 154(b) by 283 days.

(21) Appl. No.: 16/456,404

(22) Filed: Jun. 28, 2019

(65) Prior Publication Data
US 2020/0405977 A1 Dec. 31, 2020

(51) Int. Cl.
*A61M 5/32* (2006.01)

(52) U.S. Cl.
CPC ........ *A61M 5/3234* (2013.01); *A61M 5/3221* (2013.01); *A61M 5/3286* (2013.01); *A61M 5/3293* (2013.01)

(58) Field of Classification Search
CPC ........ A61B 5/150496; A61B 5/150572; A61B 5/150473; A61M 5/3293; A61M 5/3202; A61M 5/002
See application file for complete search history.

(56) References Cited

U.S. PATENT DOCUMENTS

| | | |
|---|---|---|
| 3,469,572 A | 9/1969 | Nehring |
| 4,136,794 A | 1/1979 | Percarpio |
| 4,140,108 A | 2/1979 | Nugent |
| 4,295,476 A | 10/1981 | Quaas |
| 5,122,123 A | 6/1992 | Vaillancourt |
| 5,290,254 A * | 3/1994 | Vaillancourt ......... A61M 5/326 128/919 |
| 5,312,366 A | 5/1994 | Vailancourt |

(Continued)

FOREIGN PATENT DOCUMENTS

| | | |
|---|---|---|
| DE | 20 2008 010494 U1 | 11/2008 |
| EP | 3 173 113 A1 | 5/2017 |

(Continued)

OTHER PUBLICATIONS

Extended European Search Report dated Nov. 16, 2020, which issued in the corresponding European Patent Application No. 20178859.3.

*Primary Examiner* — Nilay J Shah
*Assistant Examiner* — Robert F Allen
(74) *Attorney, Agent, or Firm* — Greenberg Traurig, LLP; David J. Dykeman; Roman Fayerberg (57) ABSTRACT

A needle hub assembly for a pen needle includes a needle hub, a cannula or needle coupled to the needle hub, a retractable and compressible sleeve covering at least one end of the cannula, and an outer cover. The outer cover encloses the needle hub and the retractable sleeve. The retractable sleeve is coupled to the hub to cover the end of the cannula where the sleeve can pass through or can be pierced by the cannula and the sleeve retracts axially on the cannula. The sleeve is resilient and returns to an original configuration when an insertion force is released. The needle hub can have a first sleeve to cover a patient end of the cannula, and second sleeve to cover a non-patient end of the cannula where the sleeves retract onto the cannula or hub and expand to the original configuration to cover the ends of the cannula.

17 Claims, 9 Drawing Sheets

(56) References Cited

U.S. PATENT DOCUMENTS

| | | | |
|---|---|---|---|
| 2011/0071492 A1* | 3/2011 | Horvath | A61M 5/326 604/506 |
| 2013/0211330 A1* | 8/2013 | Pedersen | A61M 5/2033 604/111 |
| 2018/0001033 A1* | 1/2018 | Benito | A61M 5/3202 |
| 2018/0021526 A1* | 1/2018 | Sullivan | A61M 5/349 604/506 |

FOREIGN PATENT DOCUMENTS

| | | |
|---|---|---|
| WO | 2016123494 A1 | 8/2016 |
| WO | 2017131802 A1 | 8/2017 |

\* cited by examiner

RETRACTABLE SLEEVE FOR PEN NEEDLE ASSEMBLY

BACKGROUND

Field of the Invention

The present invention is directed to medical devices for injecting a medication to a patient. The device can be a pen needle including a needle hub, which can have a patient-contacting surface or skin shaping surface, at least one sleeve covering a cannula or the needle, and an outer cover. The pen needle hub can be installed on a medication pen to administer medications to the patient.

Description of the Related Art

A medication pen for delivering self-administered medications generally includes a pen body, which houses a medication compartment, and a separate pen needle which may be attached to and detached from the pen body. The pen needle includes a needle hub having a recess on the proximal side for receiving the pen body and a proximal (non-patient end) needle accessing the medication compartment, typically piercing the septum of a medication cartridge in the pen body. The distal patient end of the pen needle includes the needle or cannula that is inserted into the injection site.

Injections may be performed in the intradermal (ID) region, the subcutaneous (SC) region and the intramuscular (IM) region. For many types of injectable medications, including insulin, the SC region is preferred for administering an injection.

Shorter needles, such as 4 mm and 5 mm needles, are adapted to achieve injection to a specified target depth in a subcutaneous region. In one aspect, the needle hub ensures that a needle is inserted to a desired target depth, regardless of the angle at which the user may approach the injection site with the medication pen or delivery device.

In certain prior art pen needles the cannula is supported in an axially positioned post on the needle hub. The post forms a narrow portion extending distally from the relatively wider portion in which the pen body is received. In other pen needles known in the art, a distal face of the needle hub placed against the injection site may have a slight taper at the edge. However, the edge of the needle hub engages the skin when the cannula is inserted at an angle, interfering with the injection. The slight taper is not functional during an injection, or is only at the edge of the distal face of the needle hub.

While the prior devices are generally suitable for the intended use, there is a continuing need for improved devices for controlling the penetration of a cannula for delivering a drug or medicament.

SUMMARY

The present invention is directed to a medical device such as an injection device. The injection device can be a pen needle hub assembly for coupling to an injection pen or other delivery device. In other embodiments, the device can be a syringe, blood collection device or other medical delivery device having a cannula or needle extending from opposite ends for transferring fluid from one area to another. The needle hub in one embodiment has a needle or cannula extending from a distal end of the hub with a retractable sleeve covering the needle or cannula that can be retracted to expose the distal end of the cannula for introducing the medication to the patient. The cannula can have a proximal end for piercing a septum on the injection pen where the proximal end is covered by a retractable sleeve on the needle hub that retracts when the needle hub is attached to the injection pen.

The pen needle in one embodiment includes needle hub, at least one sleeve covering at least a portion of the cannula, and an outer cover enclosing the needle hub and the sleeve. A seal or closure can be attached to an open end of the outer cover to enclose the needle hub and maintain the sterile condition until ready for use.

The pen needle hub assembly in one embodiment has a needle hub with a needle or cannula, a sleeve that fits over or on a portion of the needle hub to enclose the cannula. An outer cover can be included that fits over the sleeve and needle hub. A peel tab is attached to the open end of the outer cover for closing the open end of the outer cover. The needle hub in one embodiment has a body with a side wall with a top distal end and an open bottom, proximal end for connecting the needle hub to a delivery device, such as a pen needle delivery device used in insulin injection. An end wall closes the top end of the side wall and supports the cannula. The cannula has a patient end formed by a first end of the cannula extending distally from the hub. A retractable sleeve encloses the patient end of the needle and is coupled to the needle hub. The retractable sleeve is positioned against the skin of the patient at the injection site where the insertion force causes the cannula to pass through the sleeve as the cannula penetrates the skin of the patient. The sleeve is sufficiently flexible and resilient to fold and compress in the longitudinal direction of the sleeve in an accordion-like manner onto a portion of the hub to retract from the distal end of the cannula as the cannula is inserted into the patient. The resilience of the sleeve returns the sleeve to the original configuration when the cannula is withdrawn from the patient to cover the end of the needle to reduce the risk of accidental needle stick.

Another feature of the needle hub includes a body with a side wall, a top surface forming a shoulder extending perpendicular to the central axis of the needle hub, and a post, tower or upper portion extending upwardly from the top surface a distance from the shoulder. The axial face of the post can form a surface that deforms and shapes the surface of the skin of the patient during injection to control the depth of penetration of a cannula. A supporting post can be provided that extends inwardly from an inner face of the end wall with a central channel or bore to receive the cannula where a proximal end of the cannula extends into a cavity of the hub formed by the side wall. The post projects axially into the cavity of the hub a distance to support the cannula. In one embodiment, a retractable resilient first sleeve can be provided on the distal post to cover the distal end of the cannula. A retractable, resilient second sleeve in one embodiment is included on the proximal post to cover the proximal end of the cannula.

The distal sleeve can have a dimension to fit over the distal end of the needle hub to enclose a top portion of the needle hub and enclose the cannula. The retractable sleeve has a side wall having an inner dimension to fit over the end of the needle hub and the cannula and a length to cover the distal end of the cannula. The sleeve is flexible, resilient and compresses axially relative to the cannula when an insertion force is applied and the sleeve returns to the original position when the force is released.

In one embodiment of the retractable sleeve has a side wall and an end wall where the end wall has a diameter greater than a diameter of the side wall. The end wall can have a flat surface that forms a skin contact surface to assist in aligning and orienting the cannula in a selected position relative to the surface of the skin. The side wall of the sleeve can have a flared end that extends radially outward to join with the end wall. In one embodiment, the end wall of the sleeve can have thickness greater than a thickness of the side wall.

In a further embodiment, the proximal end of the hub includes a retractable second sleeve for covering the non-patient end of the cannula. The second sleeve is coupled to a proximal end of the hub to enclose the non-patient end of the cannula. The second sleeve is resilient and compressible in an axial direction on the non-patient end of the cannula when the needle hub is coupled to the delivery device and can expand to the original configuration when the needle hub is separated from the delivery device to cover the tip of the cannula.

In one embodiment a pen needle includes a hub having a side wall, a proximal open end, and an end wall at a distal closed end of the side wall, where the open end configured for coupling to a delivery pen. A distal post extends from the end wall and has an axial face, and an outer dimension less than an outer dimension of the side wall of the hub. A proximal post extends from an inner surface of the end wall and extends toward the open end of the hub. A cannula having a first end extends from a distal end of the distal post for introducing a medication to a patient. A second end of the cannula extends from the proximal post for piercing a septum on the delivery pen and is positioned in a cavity defined by the side wall. A resilient first sleeve has a closed end and an open end, where the open end is coupled to the distal end of the distal post and encloses the first end of said cannula. The first sleeve is compressible and foldable on the distal post when said cannula is inserted into a patient. A resilient second sleeve has a closed end and an open end, where the open end is coupled to the proximal post and encloses the second end of the cannula. The second sleeve is compressible and foldable on the proximal post when the hub is connected to a delivery device.

The needle hub in various embodiments can have a convex distal axial surface for shaping the axial face of the sleeve and shape the indentation of the surface of the skin during needle insertion and drug delivery. The needle hub can have an axial face with a surface area of about 5-50 $mm^2$. The surface of the axial face in one embodiment can have a convex configuration with a height of about of 0.3 to 0.7 mm and a surface area of 1-4 $mm^2$.

The needle hub can have a convex surface with a height of about 0.5 to 6.0 mm and a cannula with a length of about 4-10 mm and typically about 5-6 mm projecting from the hub. The convex surface can have a radius of curvature of about 5.0 to 8.0 mm. The cannula can be located in the center of the surface so that the surface surrounds the cannula. In one embodiment the invention, the convex surface can have a height of at least about 0.5 and typically at least about 1.0 mm relative to the outer edge of the hub and width of about 5.0 to 7.0 mm to provide sufficient surface area and a suitable shape and angle with respect to the axis of the cannula to shape the end surface of the sleeve and the skin and provide the controlled depth of penetration by the cannula into the skin. In one embodiment, the cannula can have a length of about 4.2 mm.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawing in which.

DETAILED DESCRIPTION OF THE EMBODIMENTS

A medication pen or delivery device is used herein to refer to a device having a medication compartment, typically containing multiple doses of medication, and a separate pen needle. The phrase "pen needle" refers to a needle-bearing assembly which can be attached to the medication pen body so that a proximal end of the pen needle assembly accesses a medication compartment and a distal end is adapted for insertion into an injection site to perform one or more injections. The terms "needle" and "cannula" are used herein interchangeably to refer to a hollow tubular member having a lumen and a sharpened end for insertion into an injection site on a subject. As used herein, the "distal" direction is in the direction toward the injection site, and the "proximal" direction is the opposite direction. "Axial" means along or parallel to the longitudinal axis of the needle and the "radial" direction is a direction perpendicular to the axial direction.

Reference is made to embodiments, which are illustrated in the accompanying drawings, wherein like reference numerals refer to like elements throughout. The embodiments described herein exemplify, but do not limit, the present invention by referring to the drawings. The exemplary embodiments are presented in separate descriptions, although the individual features and construction of these embodiments can be combined in any number of ways to meet the therapeutic needs of the user.

This disclosure is not limited in its application to the details of construction and the arrangement of components set forth in the following description or illustrated in the drawings. The embodiments herein are capable of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure.

Figure 1:
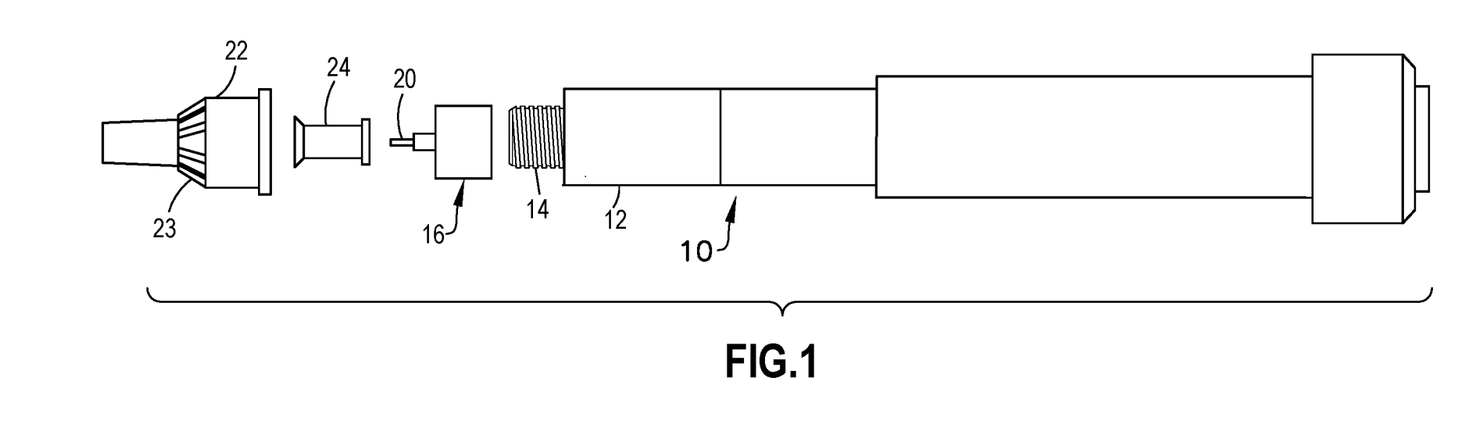
FIG. 1 is an exploded perspective view a needle hub assembly according to one embodiment.

In one embodiment the delivery device is a pen needle delivery device 10, as shown in FIG. 1, which typically comprises a dose knob/button, a body 12, and a cap. The body typically includes a threaded end 14 for coupling with pen needle hub 16. A dose knob/button allows a user to set the dosage of medication to be injected. The body 12 is gripped by the user when injecting medication. The cap is used by the user to securely hold the pen needle device 10 in a shirt pocket or other suitable location and provide cover/protection from accidental needle injury.

In standard pen needle devices the dosing and delivery mechanisms are found within the body 12 and is not described in greater detail here as they are understood by those knowledgeable of the art. A medicament cartridge is typically attached to a standard pen injector housing by known attachment mechanism. The distal movement of a plunger or stopper within the medicament cartridge causes medication to be forced into the reservoir housing. The medicament cartridge is sealed by a septum and punctured by a septum penetrating needle cannula located within a reservoir or housing. Reservoir housing is preferably screwed onto the medicament cartridge although other attachment mechanism can be used. The pen needle delivery device can be a standard pen delivery device known in the industry so that the pen needle delivery device is not shown in detail. The cannula can be a double-ended cannula 20 beveled and sharpened at both ends for coupling to the pen needle assembly and for penetrating the skin of the patient. The cannula has a lumen with a diameter sufficient to inject the medication into the patient.

Figure 2:
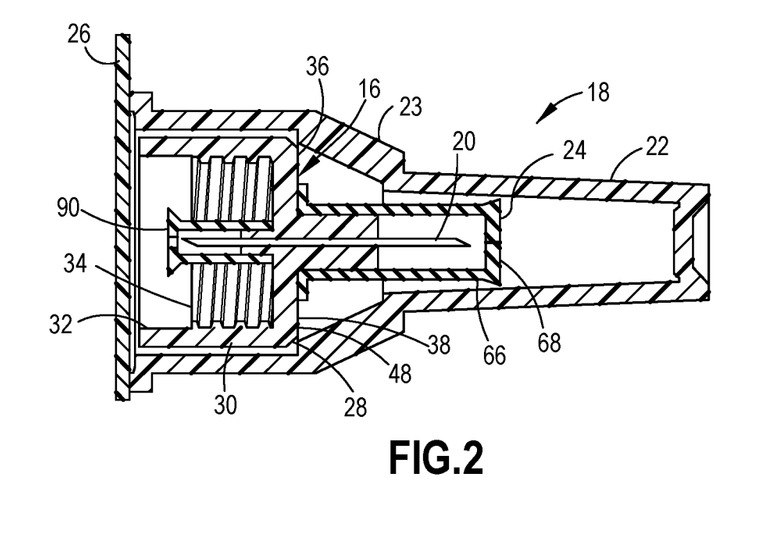
FIG. 2 is a cross section view of the needle hub assembly of FIG. 1.

The pen needle assembly 18 as shown in FIG. 2 includes a needle hub 16 supporting a hollow needle or cannula 20, a removable outer cover 22 having ribs 23, and a retractable sleeve 24. A protective seal 26 is attached to the open end of the outer cover as shown in FIG. 2 to enclose the needle hub and cannula to maintain a clean and sterile condition. The seal 26 can be a label or other closure member that can be easily peeled from the outer cover to access the needle hub during use.

Figure 8:
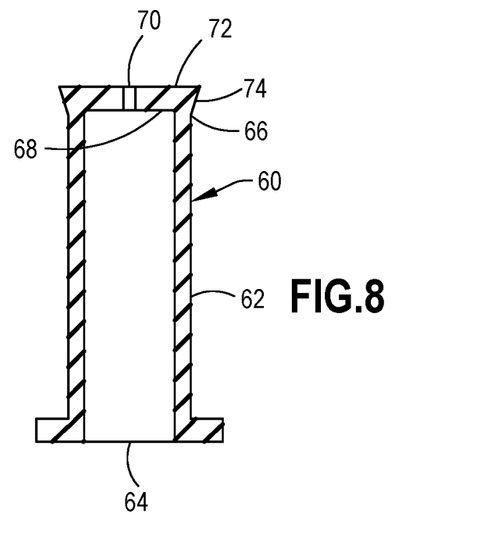
FIG. 8 is a cross sectional view of the sleeve for covering the patient end of the cannula.

In the embodiment shown in FIGS. 2-7, and 10-12, the needle hub 16 for coupling to the delivery pen has a body 28 having a side wall 30 forming an open end 32. In the embodiment shown, body 28 has a substantially cylindrical shape. The open end 32 forms an internal cavity with internal threads 34 as shown in FIG. 2 for coupling to the pen needle delivery device as shown in FIG. 8. In another embodiment, the needle hub may be provided with flattened sides to assist in rotating the needle hub and coupling the needle hub to the pen needle assembly.

The body 28 of needle hub 16 has a distal end wall 48 with a peripheral edge 36 forming a shoulder 38. The shoulder can be oriented in a plane substantially perpendicular to a central axis of the needle hub 16. A post 40 forming a first support extends from the shoulder 38 in the axial direction relative to the central axis away from the open end 32. The post 40 has a side surface extending substantially parallel to side wall 30 of body 28 of needle hub 16. The post 40 has a distal end, and an axial face 42 that can shape the surface of the skin depending on the use of the pen needle. The axial end face 42 can have a substantially flat surface as shown in FIG. 2 or a convex shape shown in FIG. 13. In an embodiment of the needle hub, the axial face 42 has a generally rounded, convex shape. The shoulder can have a width of about 1-4 mm from the peripheral edge of body 28 and side of the post 40.

A proximal post 44 forms a second support for supporting a needle or cannula and extends inwardly from an inner face 46 of end wall 48 of the hub body 28 as shown in FIGS. 2-7. Post 44 projects inwardly in the axial direction of the center axis for supporting the cannula 20. Post 44 has an axial passage extending through needle hub 16 for receiving and supporting the cannula 20. In the embodiment shown, the proximal post 44 projects into the cavity formed by the side wall of the body of the hub a distance sufficient to support the cannula without interfering with the connection to the delivery device.

The cannula 20 as shown is a double ended cannula secured in the axial passage of the post 40 and the post 44. The cannula 20 has a distal end portion 50 extending from the distal end of the post 40 a distance to provide a desired depth of penetration into the patient. The exposed length of the distal end portion 50 extending from the distal end of the post 40 can have a length of about 4-10 mm and generally about 4-6 mm. The exposed length of the distal end of the cannula can be selected to provide a selected depth of penetration of the cannula. The cannula 20 terminates at a sharpened tip 52 at a distal end. The distal end portion of the cannula forms the patient end of the cannula.

The cannula 20 has a proximal end portion 54 terminating at a sharpened proximal tip 56 as shown in FIG. 2. The proximal end portion 54 extends from the proximal post 44 a distance for piercing the septum of the delivery device. The proximal end portion of the cannula forms a non-patient end of the cannula. Although a single cannula is shown having the opposite ends with a sharpened tip, separate needles or cannulas can be mounted on the hub to form the patient end and the non-patient end.

A retractable sleeve 60 is coupled to the needle hub 16 to enclose the distal portion end 50 of the cannula 20 as shown in FIG. 2. The sleeve 60 in the embodiment shown in FIGS. 3-5 has a length and width to enclose the distal end portion 50 of the cannula 20 and can retract to expose the distal end portion 50 for piercing the skin of the patient and delivering the medication to the patient. The retractable sleeve 60 can expose a selected length of the distal end portion 50 to provide the desired depth of penetration.

The retractable sleeve 60 in the embodiment shown has a side wall 62 with an open end 64 and a closed end 66 formed by an end wall 68. In the embodiment of FIG. 2, the end wall 68 completely closes the end of the sleeve 60. An opening 70 is provided in the end wall 68 in the embodiment of FIGS. 3-6 as shown and having a dimension for allowing the cannula to pass through. The opening 70 in one embodiment can have a dimension corresponding to the outer diameter of the distal post. In other embodiments, the end wall 68 can be closed and solid with no opening and has a thickness to enable the cannula to pierce the end wall as the cannula penetrates the skin of the patient. In one embodiment, the opening can be a slit formed in the end wall 68 shown in FIG. 2 to assist the cannula in passing through the end wall of the sleeve and reduce the risk of coring the end wall and obstructing the lumen in the cannula.

The side wall 62 in one embodiment can have a substantially cylindrical shape with a length to cover the exposed length of the distal end portion 50 of the cannula 20. The side wall 62 of the sleeve 60 can have an outer diameter of about 3-6 mm and generally about 3-5 mm. The open end 64 has an inner dimension complementing the outer dimension of the post 40 to fit onto the post 40 as shown in FIG. 2. In one embodiment, a flange can be positioned to contact the shoulder 38 of the hub to stabilize the sleeve 60. The sleeve can have an inner diameter complementing the outer dimension of the hub 16 that supports the cannula and sleeve. The sleeve in the embodiment shown is attached to the post and retracts onto the post where the side wall of the sleeve does not contact the outer surface of the cannula.

Figure 3:
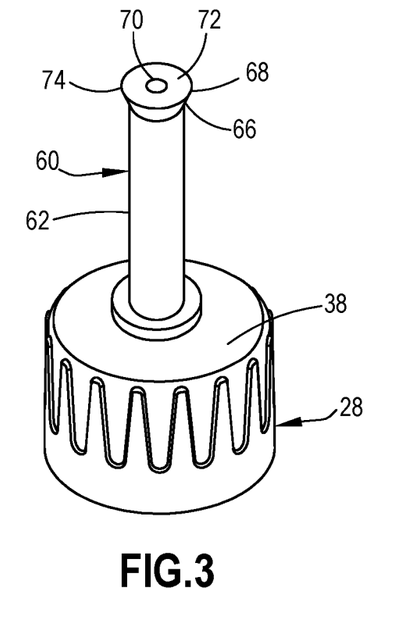
FIG. 3 is a perspective view of the needle hub and sleeve in the embodiment of FIG. 2.
Figure 4:
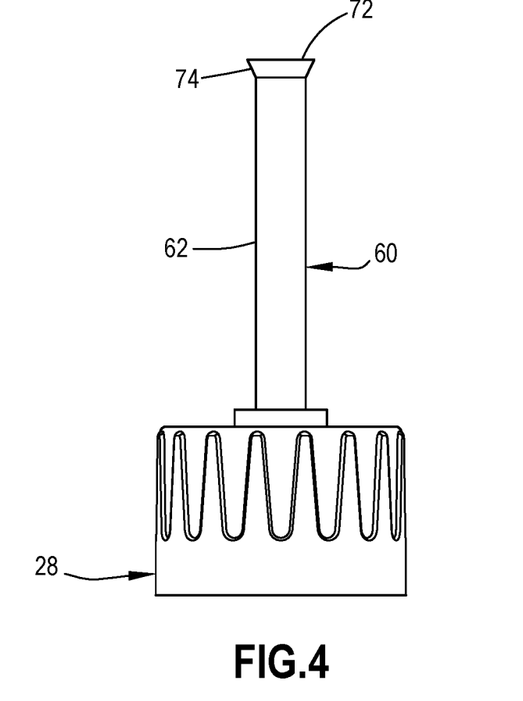
FIG. 4 is a side view of the needle hub and sleeve of FIG. 3.
Figure 5:
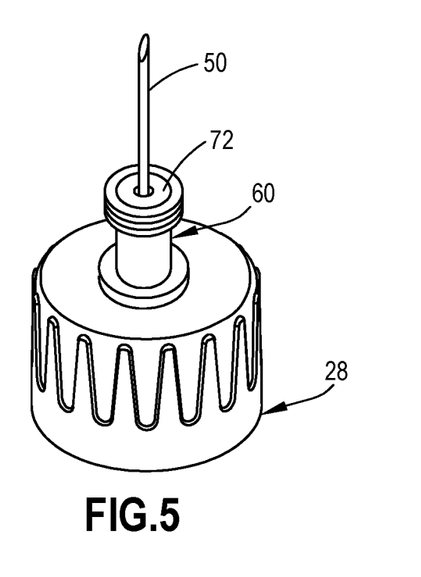
FIG. 5 is a perspective view of the needle hub and sleeve of FIG. 3 with the sleeve in the retracted position.
Figure 6:
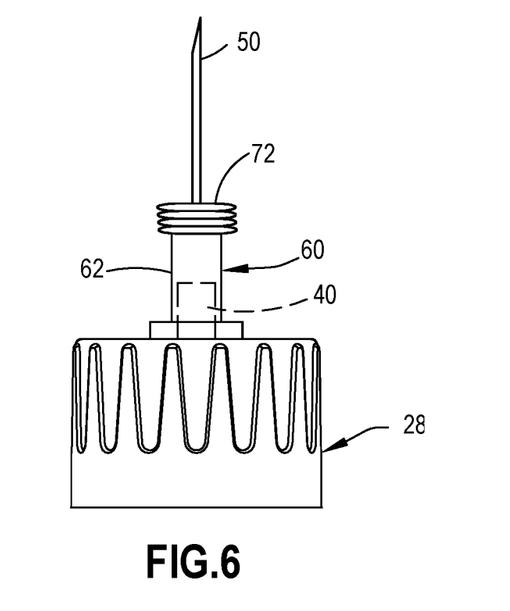
FIG. 6 is a side view of the needle hub and retracted sleeve.
Figure 7:
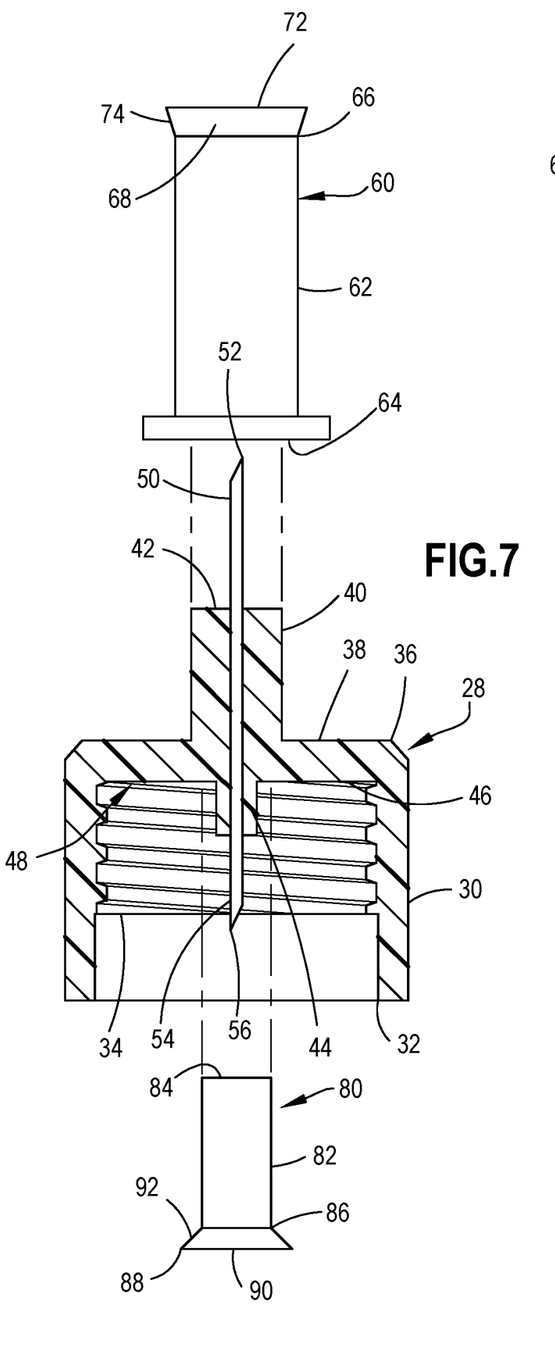
FIG. 7 is an exploded side view of the needle hub assembly showing the needle hub, distal sleeve, and proximal sleeve.

In the embodiment shown, the end wall 68 of the sleeve 60 has an outer peripheral edge coupled to the side wall 62. In one embodiment, the end wall 68 has a circular shape corresponding to the cylindrical shape of the side wall 62. The end wall 68 can have an outer diameter greater than an outer diameter of the side wall 62 as shown in FIG. 2. In the embodiment shown in FIGS. 3-8, the end wall 68 has an opening 70 aligned with the needle 20 and has a dimension to enable the needle 20 to pass through the opening 70. The distal end portion of the side wall 62 has an outwardly flared end portion 74 that converges with and is proximate the end wall 68 and an axial end face 72 of the end wall 68. The axial face 72 in one embodiment is substantially flat and lies in a plane substantially perpendicular to the longitudinal axis of the sleeve 60 as shown in FIG. 3. The axial face 72 can have a width of about 1.2 to about 1.4 times the outer diameter of the side wall 62. In other embodiments, the axial face 72 can be curved with a convex configuration or have a concave surface for contacting the skin of the patient during the injection.

The side wall 62 of the sleeve 60 has a thickness to provide the flexibility of the sleeve to deflect and compress along the axial length of the cannula when the cannula pierces the skin of the patient. The end wall 68 in the embodiment shown has a thickness that is thicker than the thickness of the side wall 62. The thickness of the end wall 68 is typically sufficient to provide a stable shape to the end wall when positioned against the surface of the skin of the patient and during the insertion of the cannula into the patient. The thickness of the end wall 68 can be about 1.5 to 3 times the wall thickness of the side wall 62. In one embodiment, the end wall 68 has a thickness of about 1.5 to 2.0 times the wall thickness of the side wall. The thickness of the end wall can depend on the dimension of the sleeve and the dimensions of the cannula. The end wall has a thickness and the opening 70 and has a dimension to allow the cannula to pass through the end wall without requiring an excessive insertion force to pass through the end wall and penetrate the skin of the patient.

Figure 9:
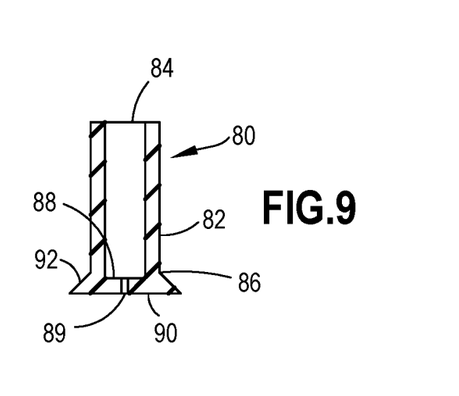
FIG. 9 is a cross-sectional side view of the sleeve covering the non-patient end of the cannula of FIG. 1.

A second retractable proximal sleeve 80 is coupled to the needle hub 16 to cover the proximal end portion 54 of the cannula 20. The sleeve 80 as shown in FIGS. 8 and 9 has a substantially cylindrical shaped side wall 82 with an open end 84 and a closed end 86. The closed end 86 includes an end wall 88. The end wall 88 in the embodiment shown has a substantially flat axial face 90 and diameter greater than an outer diameter of the side wall 82. In one embodiment, the end wall 88 has an opening 89 to allow the cannula to pass through. The opening 89 can have a dimension corresponding to the diameter of the proximal post. The end portion of the side wall 82 has a flared portion 92 diverging outward to join the axial face of the end wall 88. The end wall 88 generally has a thickness greater than a thickness of the side wall 82. The end wall 88 can have a thickness of about 1.5 to 2.5 time the thickness of the side wall and typically about 1.5 to 2.0 times the thickness of the side wall. The side wall 82 has a thickness to maintain the shape to over the proximal end of the cannula 20 and be able to compress axially relative to the cannula 20 and spring back to the original shape when the compression force is released. The sleeve 80 is coupled to the proximal end of the needle hub 16 and is supported by the hub.

The sleeve 80 in one embodiment is coupled by a friction fit to the proximal post 44 and extends from the proximal end of the hub 16. The sleeve 80 extends a distance from the post 44 to cover the proximal end of the cannula 20. The sleeve 60 and sleeve 80 are made of the flexible and resilient polymeric material, such as an elastomer. The elastomeric material is able to compress and fold axially to expose the cannula during use and spring back to the original configuration to cover the ends of the cannula after use to reduce the risk of needle stick. In one embodiment, the sleeves can be self-sealing after returning to the original shape to prevent leakage of the fluids from the cannula.

Figure 10:
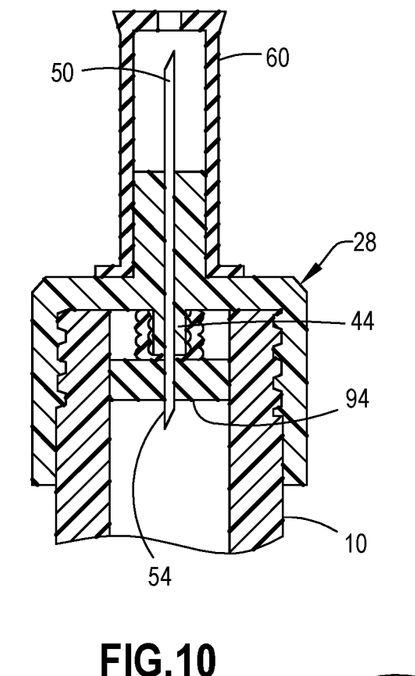
FIG. 10 is a cross sectional side view of the needle hub of coupled to a delivery device.

During use of the pen needle, the needle hub 16 is connected to the pen needle delivery device 10. The seal 26 shown in FIG. 2 is removed to expose the open proximal end of the hub 16. The hub 16 is connected to the pen needle delivery device 10 by screwing the hub onto the threaded end of the delivery device as shown in FIG. 10. Typically, the outer cover 22 is used to grip the hub during the connecting step and is removed after the hub is properly connected to the delivery device. The axial end face 90 of the sleeve 80 initially contacts the septum 94 in the delivery device 10. The threading of the hub 16 onto the threaded end 14 compresses the sleeve 80 axially in an accordion-like manner until the proximal end portion 54 of the cannula 12 pass through the end wall 88 of the sleeve. The proximal end portion 54 of the cannula 20 continues advancing to pierce the septum 94 to provide a fluid connection between the hub 16 and the delivery device 10. The sleeve 80 compresses and folds axially in an accordion-like manner and retracts relative to the cannula onto the post 44 as shown in FIG. 10. The sleeve 80 is sufficiently flexible and resilient to compress and retract onto the post by an axial force and return to the original orientation when the hub is separated from the delivery device to cover the proximal end of the cannula as shown in FIG. 2 so that the used needle hub can be discarded safely.

Figure 11:
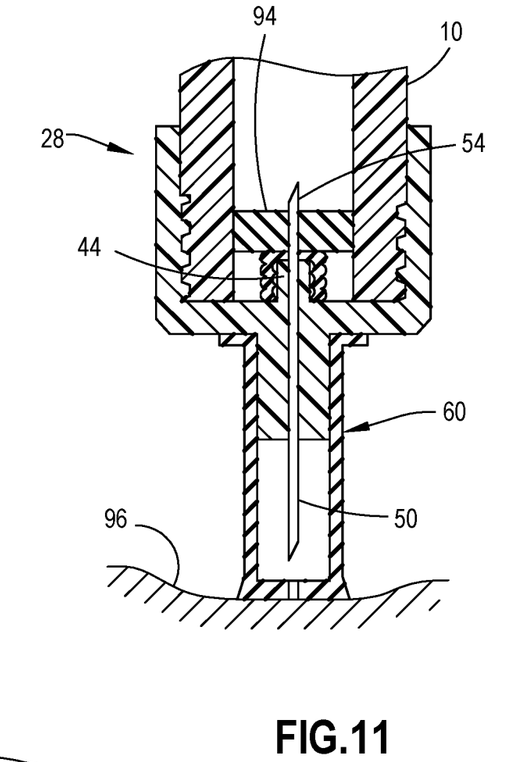
FIG. 11 is a cross sectional view of the needle hub showing the sleeve on the distal end of the needle positioned against the skin of the patient.
Figure 12:
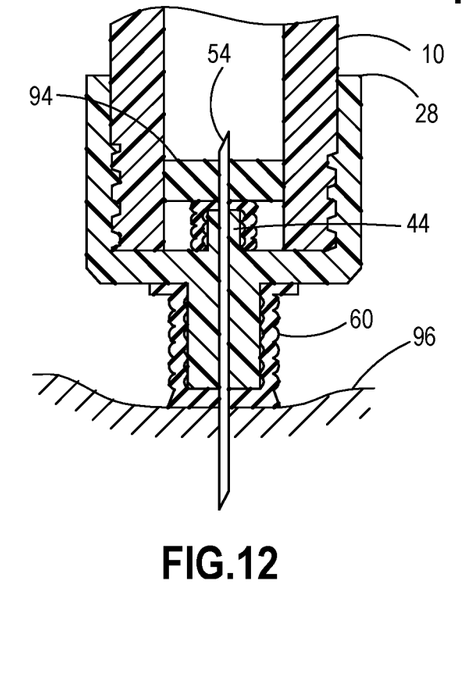
FIG. 12 is a cross sectional side view of a needle hub showing the sleeve on the distal end of the needle in the retracted position.

After the needle hub 16 is coupled to the delivery device 10, the outer cover 22 can be removed to expose the sleeve 80 covering the distal end portion 50 of the cannula 20. The end wall 88 of the sleeve 80 can be placed against the surface of the skin 96 of the patient as shown in FIG. 11. The axial end face 90 provides a sufficiently wide surface area to assist the user in placing the axial face of the sleeve against the surface of the skin and orient the needle hub and delivery device in a selected orientation, such as substantially perpendicular to the surface of the skin for the injection. An insertion force is applied to the delivery device where the cannula pass through the end wall 88 to pierce the skin of the patient. The flexible properties of the sleeve 88 compress the sleeve axially as the cannula is inserted into the skin where the sleeve retracts onto the post 40 as shown in FIG. 12. The sleeve is able to compress and retract in an accordion-like manner to enable the length of the cannula to pierce the skin to a selected depth. The end of the sleeve conforms to the shape of the axial end of the post when contacting the skin. The insertion force forms an indentation in the surface of the skin as shown in FIG. 10 where the dimension and shape of the end wall of the sleeve and the post control the depth of penetration of the cannula. After the injection, the cannula is withdrawn from the patient and the sleeve 60 expands to the original configuration to cover the tip of the cannula to reduce the risk of inadvertent needle stick. The needle hub can be removed from the delivery device and discarded in a suitable waste container.

Figure 13:
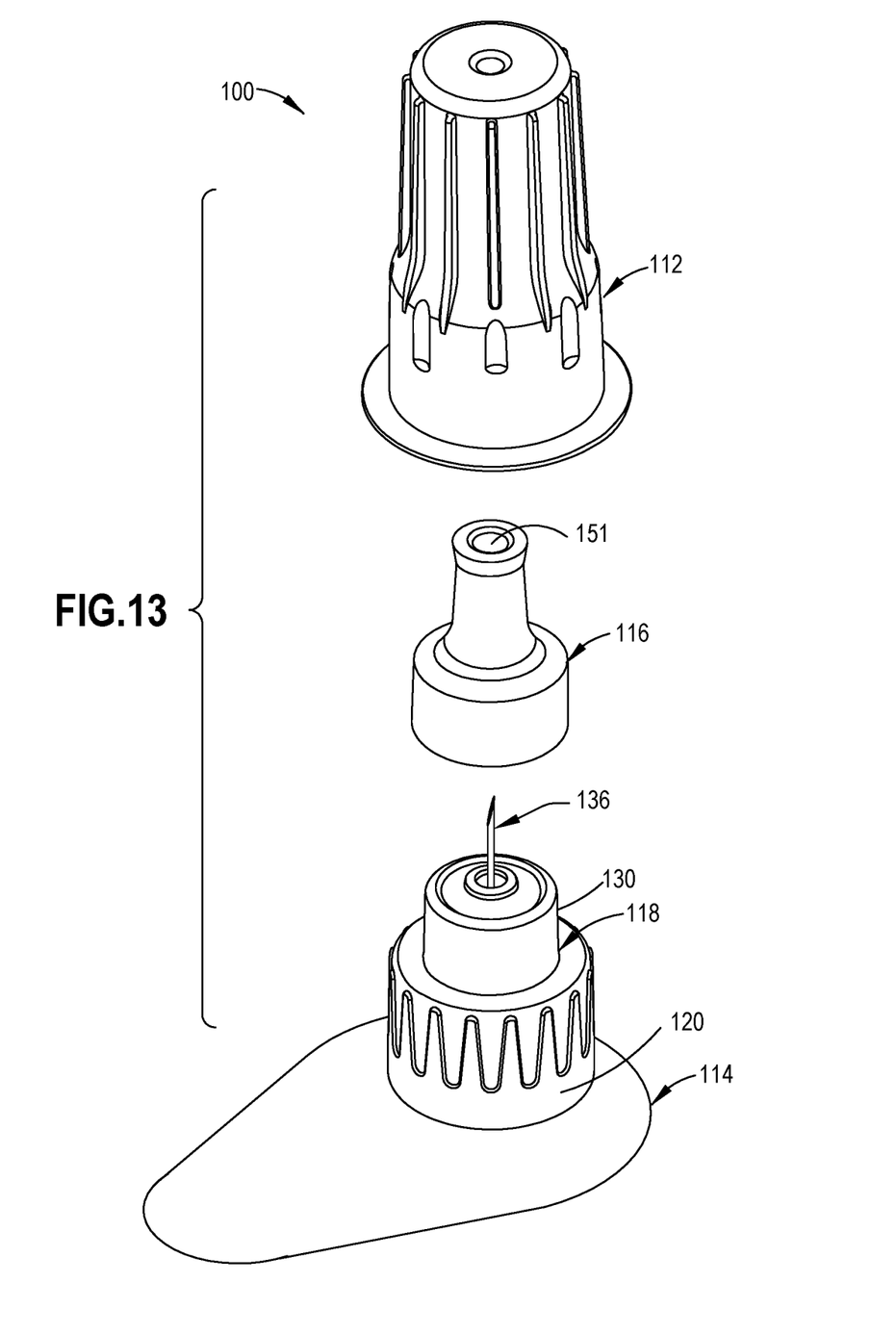
FIG. 13 is an explode of the needle hub in another embodiment.

FIGS. 13-23 illustrate a second embodiment of the pen needle device. FIG. 13 is an exploded view of the pen needle assembly 100, which includes an outer cover 112, a seal 114 attached to the open end of the cover 112, a needle hub 118, and flexible retractable sleeve 116. The outer cover 112 and the seal 114 are as in the previous embodiment and are not described in detail.

Figure 14:
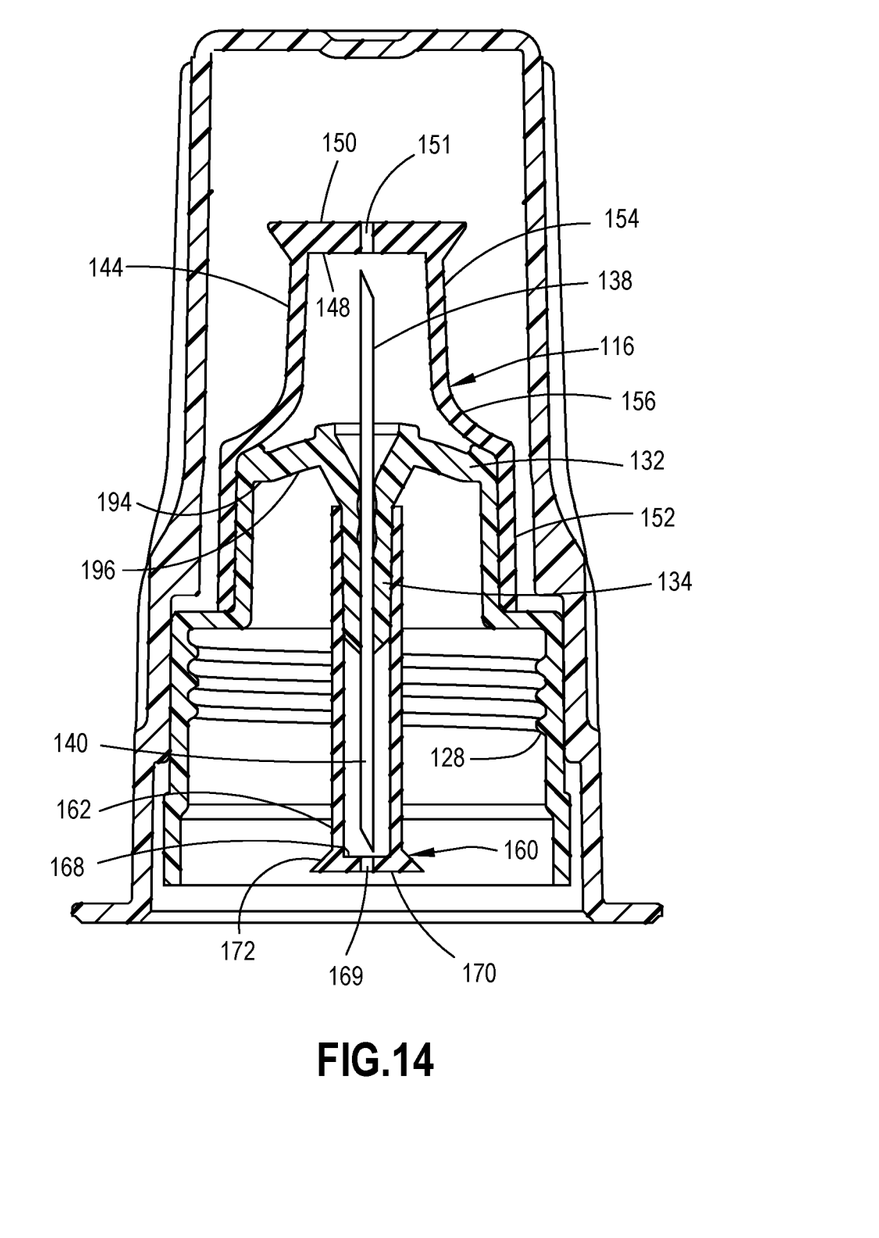
FIG. 14 is a cross sectional view of the needle hub of FIG. 13.
Figure 15:
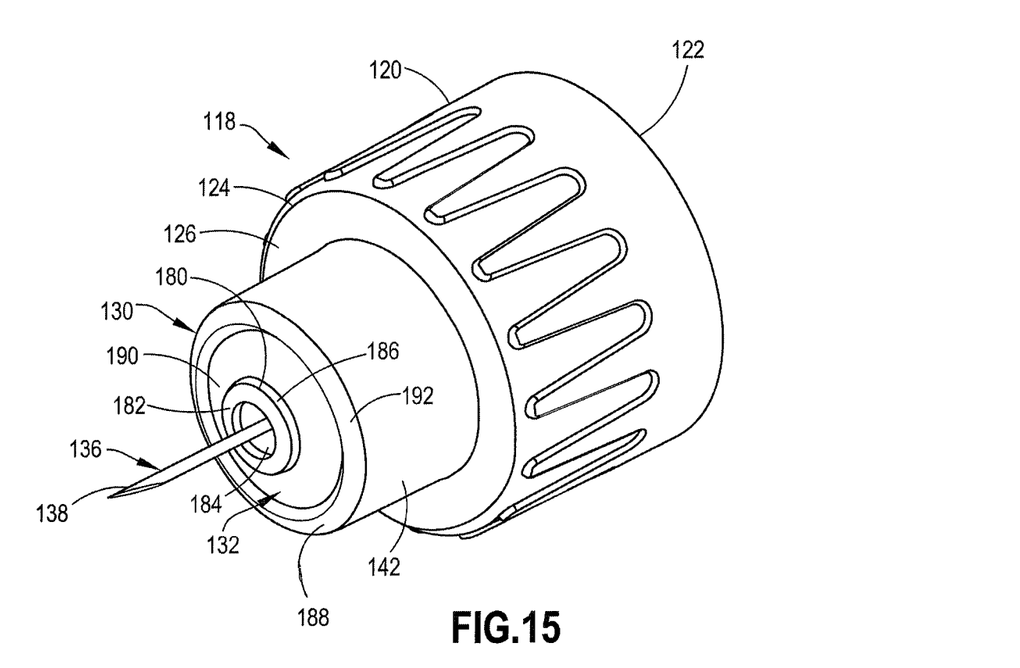
FIG. 15 is a perspective view of the contact face of the needle hub of FIG. 14.
Figure 16:
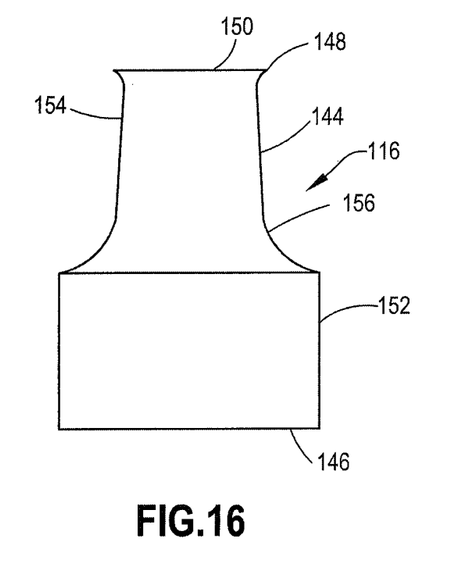
FIG. 16 is a side view of the sleeve on the patient end of the needle hub.
Figure 17:
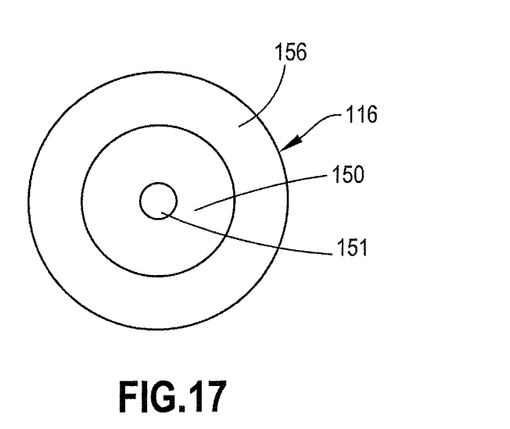
FIG. 17 is an end view of the sleeve of FIG. 16.

The needle hub 118 in the embodiment shown has a side wall 120 with an open end 122 and a closed end 124 formed by an end wall 126. An inner surface of the side wall 120 includes internal threads 128 for connecting with the delivery device as known in the art. The end wall 126 extends inwardly from the side wall to form a shoulder. A post 130 having a tower-like configuration extends from the end wall 126 as shown in FIG. 14 and FIG. 15. The post 130 terminates with an end wall 132 forming a distal end and axial face of the needle hub. An inwardly extending post 134 projects from the inner surface of the end wall as shown in FIG. 14. The post 134 has an axial passage configured for supporting a cannula 136 in the needle hub.

The cannula 136 extends through the passage of the post 134 with a distal end 138 extending from the distal face of the post 130 and has a length sufficient to introduce the medication to a selected depth into the skin of the patient. A proximal end 140 extends from the proximal end of the post 134 to project into a cavity formed by the side wall of the needle hub. The proximal end has a length to pierce the septum in the delivery device to provide fluid communication from the delivery device to the needle hub.

The sleeve 116 in the embodiment shown is coupled to the post 130 to cover the distal end of the cannula. The sleeve 116 can be attached to a side wall 142 of the post 130 by a friction fit or by an adhesive. The sleeve 116 has a side wall 144 with an open end 146 mounted on the post 130, and a closed distal end 148. The proximal end of the sleeve 116 can have an outer diameter of about 8 to 12 mm.

The sleeve has an end wall 148 closing the end of the sleeve. The end wall in the embodiment shown has a substantially flat axial face 150 extending perpendicular to the axis of the cannula and needle hub and an opening 151 aligned with the cannula to allow the cannula to pass through. The end wall 148 and the axial face have a diameter and width greater than a diameter of the distal end of the side wall 144 of the sleeve 116. The end wall 148 has a thickness greater than a thickness of the side wall 144. As shown in FIG. 14, the closed end of the side wall 144 of the sleeve diverges outwardly to form a flared end portion that joins the end wall and the axial face. The axial end face 150 can have a diameter of about 3 to 7 mm and generally about 3 to 5 mm.

In the embodiment shown, the side wall at the open end has a proximal portion 152 with a substantially cylindrical cross sectional configuration with a substantially uniform wall thickness and flexibility. The proximal end portion 152 of the sleeve 116 in the embodiment of FIG. 14 has a width greater than the distal end portion 154 of the sleeve. The proximal end portion 152 has an internal surface configured for coupling with the post by a friction fit as shown in FIG. 14. A flared middle portion 156 extends between the proximal portion 152 and the distal end portion 154 of the sleeve to form a substantially conical shape where the end wall 148 has a width less than the width of the middle portion 152 and less than the open end and the distal end portion 154. In other embodiments, the sleeve 116 can have a substantially cylindrical side wall as in the previous embodiment, where the end wall has a width corresponding substantially to the diameter of the post 134 where the end wall of the sleeve can conform to the shape and contour of the distal face of the post 134 when pressed against the skin of the patient.

Figure 18:
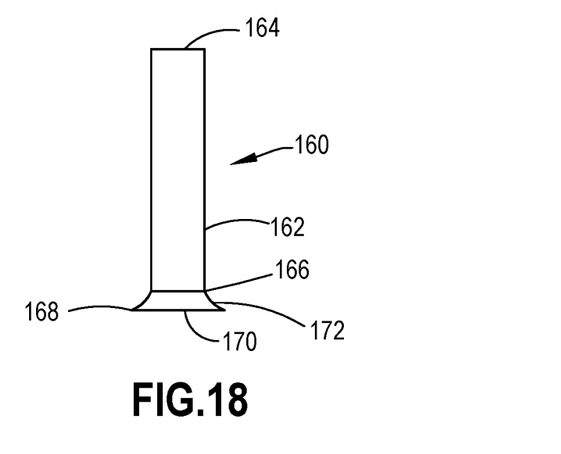
FIG. 18 is a side view of the sleeve of the non-patient end of the cannula.
Figure 19:
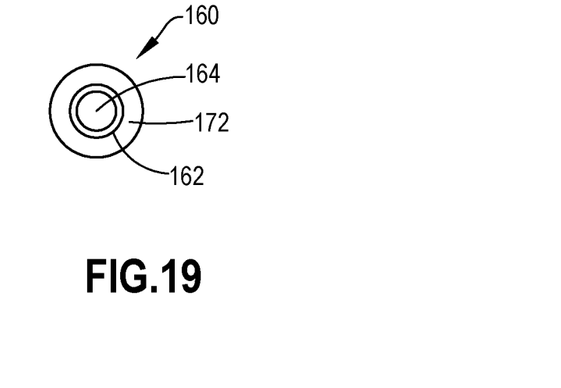
FIG. 19 is an end side view of the sleeve of FIG. 18.

A proximal retractable sleeve 160 is included to cover the proximal end 140 of the cannula 136 in a manner similar to the previous embodiment. As shown in FIGS. 18 and 19, the sleeve 160 has a substantially cylindrical side wall 162 with an open end 164 and a closed end 166 with an end wall 168. The end wall 168 in the embodiment shown has an opening 169 with a dimension to allow the cannula to pass through without obstruction. The end wall 168 as in the previous embodiment has an axial face with a diameter greater than a diameter of the outer surface of the side wall 162 and the end wall has a thickness greater than a thickness of the side wall 162. The closed end portion of the side wall 162 has an outwardly flared end 172 to define an axial face 170 of the end wall 168 having a diameter greater than the diameter of the side wall.

Figure 20:
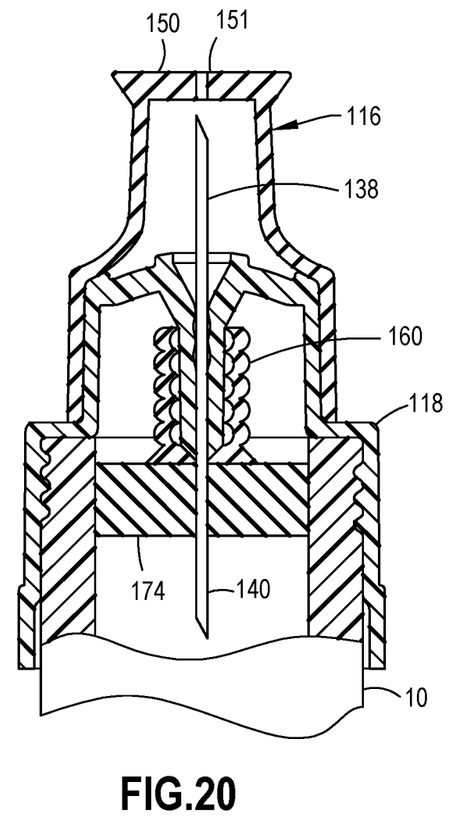
FIG. 20 is a cross sectional view of the needle hub coupled to the delivery device.

The needle hub 118 is connected to the delivery device in a manner similar to the previous embodiment by threading the open end 122 of the hub 118 onto the delivery device 10 as shown in FIG. 20. The end of the sleeve 160 engages the septum 174 of the delivery device to compress the end of the sleeve 160 into contact with the cannula 136 where the proximal end 140 of the cannula 136 pass through the end wall 168 of the sleeve 160. The proximal end 140 of the cannula continues through the end wall of the sleeve to pierce the septum 174 to provide fluid communication between the delivery device and the needle hub. The sleeve 160 compresses axially onto the post 134 in an accordion-like manner to collapse onto the post as shown in FIG. 20.

Figure 21:
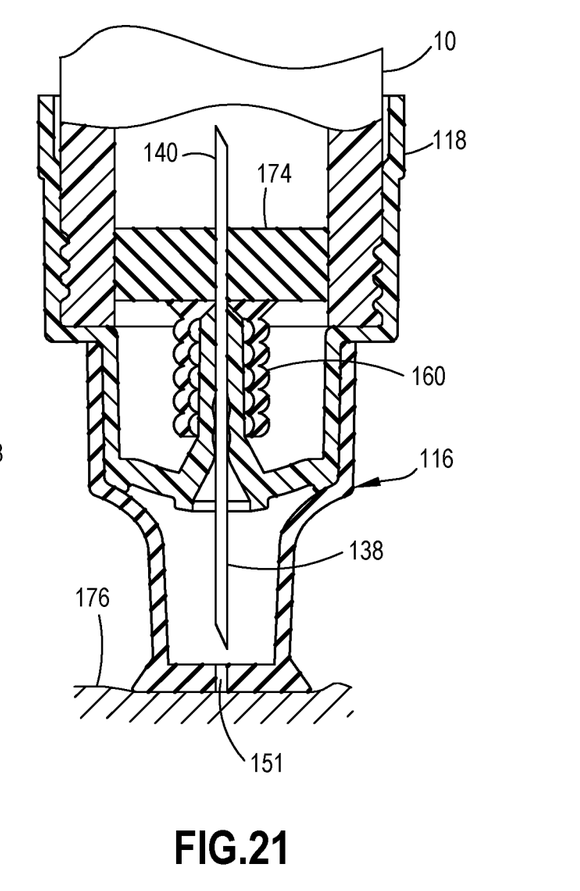
FIG. 21 is a cross sectional view of the sleeve positioned against the skin of the patient.
Figure 22:
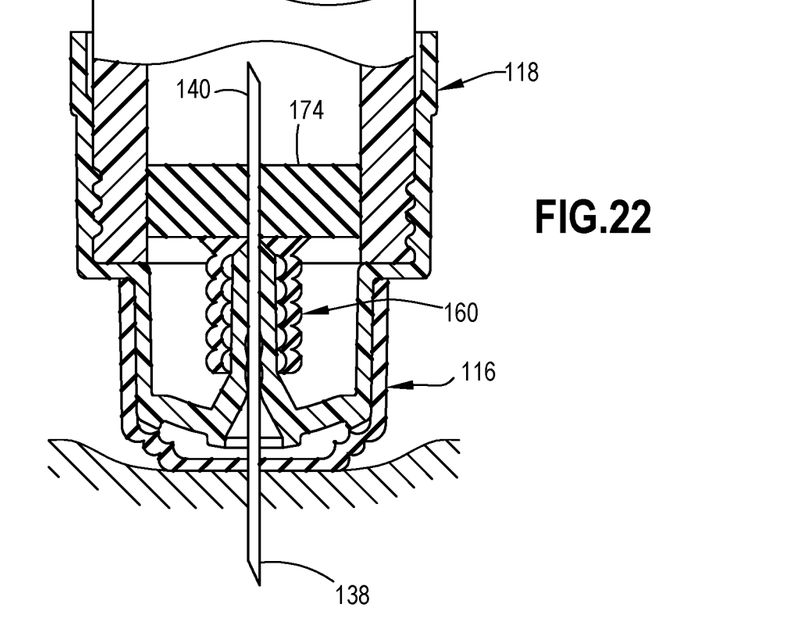
FIG. 22 is a cross sectional view of the sleeve retracted during the insertion into the patient.
Figure 23:
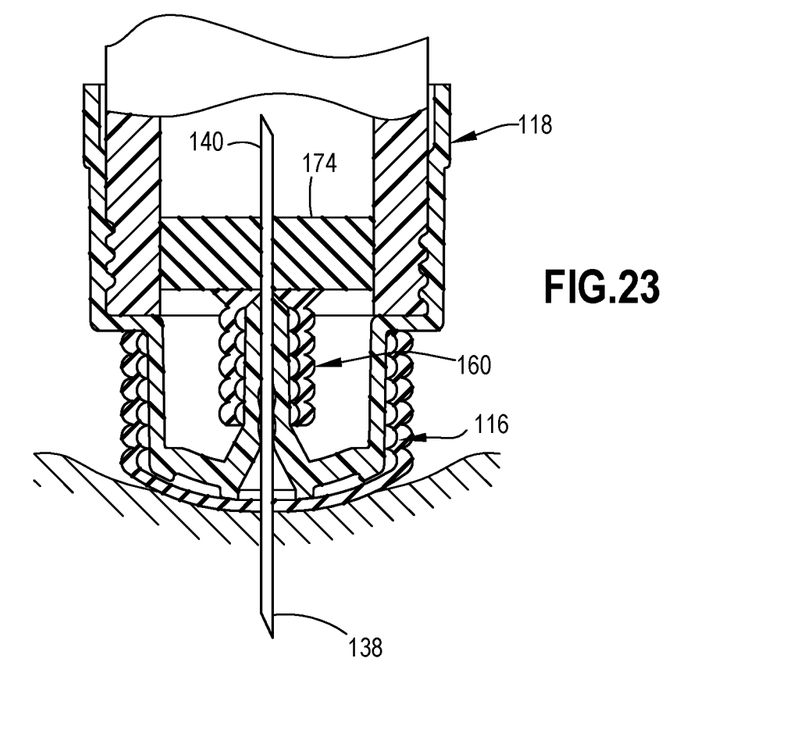
FIG. 23 is cross sectional view of the cannula inserted into the skin of the patient.

After the needle hub is connected to the delivery device, the outer cover can be removed to expose the distal sleeve 116 for delivering the medication to the patient. The flat axial face 150 of the sleeve 116 is positioned against the surface of the skin 176 of the patient as shown in FIG. 21. The flat axial face of the sleeve can assist the user in orienting the needle hub substantially perpendicular to the surface of the skin and resists sliding movement on the skin as the proximal end of the cannula pierces the skin. The sleeve 116 compresses and retracts onto the outer surface of the post 130 as shown in FIG. 22 where the end wall 148 of the sleeve contacts the skin of the patient. The insertion force of the needle hub collapses the sleeve into contact with the end wall of the post 130 where the end wall 148 of the sleeve 116 conforms to the shape and configuration of the post 130 as shown in FIG. 23.

The needle hub 118 as shown in FIGS. 13-23 can be configured to deform the skin in a controlled manner by the insertion force during the insertion and penetration of the cannula by an insertion force normally applied by the patient to control the deformation of the skin and control the depth of penetration of the cannula. The diameter, contour, and radius of curvature are selected to control the width and depth of the indentation in the surface of the skin by the cannula insertion force and control the depth of penetration of the cannula.

In the embodiment shown, the axial distal face of the needle hub 118 has a raised inner ring 180 extending from the distal face of post 130. Inner ring 180 has an axially facing distal face 182 surrounding a well 184 and cannula 136 with an inner side surface 186. A raised outer ring 188 is formed at the outer peripheral edge of the post 130 forming a recess 190 between the inner ring 180 and the outer ring 188. The outer ring 188 has an axially facing distal face 192 with an inner surface 194 facing the inner side surface 186 in the inner ring 180. In the embodiment shown, the surface of recess 190 and the axial faces of inner ring and outer ring have a substantially continuous, concentric radius of curvature and define a convex surface of needle hub 118. Recess 190 has a depth so that the skin of the patient can deflect into the recess and conform to the bottom surface of the recess during needle insertion to deform the skin in a controlled manner, thereby controlling the depth of penetration of the cannula. In one embodiment, the radial width of the recess is substantially equal to the combined radial width of the inner ring and the outer ring. The axial surface of the distal face of post 130 has a convex dome shape where the inner ring is spaced axially outward relative to outer ring and the axially facing surface of recess.

The initial penetration of the cannula 136 causes the axial face of the sleeve 116 to contact of the inner ring projecting from the post with the skin of the patient to form a depression in the skin and an initial cannula penetration depth. The axial face of the sleeve conforms to the contour and configuration of the distal end of the hub so that surface of the skin conforms substantially to the shape of the contact surface formed by the outer ring, the inner ring, and the recess and limits the depth of penetration of the cannula 136. The shape, surface area and height of the surface of the needle hub and the shape of the sleeve conforming to the end of the needle hub provide a controlled depth of penetration of the cannula during the insertion and penetration force being applied to the injection device. In the embodiment illustrated, the axial face of the end wall has a diameter at least equal to the diameter of the inner ring. In a further embodiment, the axial face of the end wall has a diameter at least equal to the outer diameter of the outer ring to conform to the shape of the axial face of the post when pressed against the surface of the skin.

During penetration of cannula 136, axial end wall of the sleeve conforms to the end wall of the post and contacts the skin of the patient. Ribs 196 can be included on inner surface of the end wall to provide sufficient strength to the end wall to resist deflection and deforming of the end wall inwardly into the cavity and resist collapsing of the conical shape of end wall when an excess insertion force is applied to the end wall. The ribs 196 also provide sufficient strength so that end wall is sufficiently rigid to prevent an outward deflection or distortion of the end wall when a pulling force is applied that may cause failure of the adhesive and provide a predetermined pull force for removal of the cannula. In the embodiment shown, four ribs are provided although the number of ribs can vary depending on the stiffness of the end wall.

The surface of the distal face of the post in the embodiment shown has a substantially convex or conical shape forming a continuous and uniform curvature extending from the outer edge of post 130 of the needle hub 118 to the distal end or outermost portion of the needle hub and the cannula so that the surface has a substantially convex, semispherical, or dome shape where the axial face of the sleeve conforms to the shape of the post when the sleeve contacts the skin during penetration of the cannula and delivery of the drug. The convex surface of the axial face of the post for deforming the surface of the skin when pressed against the skin can have a width or diameter of greater than 3.0 mm and typically about 5.0 to 8.0 mm and a height of about 0.5 to about 1.5 mm measured from the outer peripheral edge of the surface to the outermost center portion of the surface surrounding the cannula and spaced axially from the peripheral edge. In another embodiment, the convex surface has a radius of curvature of about 5.0 to 8.0 mm. In one embodiment the convex surface has a height of about 1.0 mm and a diameter of about 7.0 mm. The convex surface can have a radius of curvature of 6.0 to 16.0 mm. In various embodiments of the invention, the convex surface has radius of curvature of 6.0 to 9.0 mm. In other embodiments, the convex surface can have a radius of curvature of 6.0 to 7.0 mm. In one embodiment, the convex surface has a radius of curvature equal to or greater than the diameter of the surface. The radius curvature can be about 1 to 1½ times the diameter of the convex surface.

The ratio of the diameter (D) to the height (H) of the surface influences the depth of penetration of the cannula on insertion into the skin. Generally, the larger the ratio provides more surface area of the sleeve that will contact the skin and greater control of the depth of penetration. A smaller ratio D:H provides a smaller surface area that can compress the skin on insertion and result in a deeper penetration of the cannula. In certain embodiments, the ratio of the diameter to the height of the surface area can range from about 2:1 to 10:1. In other embodiments the ratio can range from about 5:1 to 8:1. The shape and contour of the axial face of the post controls the shape and contour of the end wall of the sleeve when pressed against the surface of the skin.

The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

The invention claimed is:

1. A pen needle comprising:
a needle hub having a side wall with internal threads, an open proximal end for coupling with a delivery device for delivering a medication, a distal end opposite said open proximal end, and a cannula having a first end extending from said distal end for introducing the medication to a patient, and said cannula having a second end extending in a proximal direction and configured for piercing a septum of the delivery device;
a resilient first sleeve having an end wall and an open end, said open end of said resilient first sleeve coupled to said distal end of said needle hub and enclosing said first end of said cannula, wherein said cannula passes through said end wall of said resilient first sleeve and said resilient first sleeve retracts in a longitudinal direction with respect to said first end of said cannula when said first end of said cannula is inserted into the patient, said end wall of said resilient first sleeve has a diameter and a thickness to conform to a skin surface of the patient when said end wall of said resilient first sleeve contacts the skin surface;
a resilient second sleeve having an end wall and an open end, said open end of said resilient second sleeve coupled to said proximal end of said needle hub and covering said second end of said cannula, wherein said cannula passes through said end wall of said resilient second sleeve and said resilient second sleeve retracts in a longitudinal direction with respect to said second end of said cannula when said needle hub is threaded onto the delivery device; and
a distal post extending from said distal end of said needle hub and having a side surface spaced inwardly from said side wall of said needle hub, and where said resilient first sleeve is coupled to said side surface of said distal post and where said resilient first sleeve is compressible and foldable onto said distal post where said end wall of said resilient first sleeve contacts and conforms to an axial face of said distal post.

2. The pen needle of claim 1, wherein;
said end wall of said resilient first sleeve has an opening with a dimension to allow said first end of said cannula to pass through and said end wall of said resilient second sleeve has an opening with a dimension to allow said second end of said cannula to pass through.

3. The pen needle of claim 2, wherein said cannula passes through said end wall of said resilient first sleeve and said resilient first sleeve retracts on said needle hub with respect to said first end of said cannula when said cannula is inserted into the patient, and said second end of said cannula passes through said end wall of said resilient second sleeve and said resilient second sleeve retracts on said needle hub with respect to said second end of said cannula when said needle hub is coupled to the delivery device.

4. The pen needle of claim 3, wherein said resilient first sleeve is configured to expand to cover said first end of said cannula when said cannula is removed from the patient.

5. The pen needle of claim 4, wherein said resilient second sleeve is configured to expand to cover said second end of said cannula when said needle hub is separated from said delivery device.

6. The pen needle of claim 1, wherein resilient said first sleeve is compressible and foldable in a longitudinal dimension and can be pierced by said first end of said cannula to expose said first end of said cannula when a cannula insertion force is applied against the skin of the patient, and said resilient second sleeve is compressible and foldable in a longitudinal dimension and can be pierced by said second end of said cannula to expose said second end of said cannula when said needle hub is connected to the delivery device.

7. The pen needle of claim 1, wherein said resilient first sleeve has a side wall, and where the thickness of said end wall of said resilient first sleeve is 1.5 to 2 times greater than a thickness of said side wall of said resilient first sleeve.

8. The pen needle of claim 7, wherein the diameter of said end wall of said resilient first sleeve is greater than a diameter of said side wall of said resilient first sleeve.

9. The pen needle of claim 8, wherein
said end wall of said resilient first sleeve has the diameter and the thickness to form a skin contact surface for stabilizing said pen needle during insertion of the cannula into the patient.

10. The pen needle of claim 9, wherein
said end wall of said resilient first sleeve is substantially flat and oriented in a plane substantially perpendicular to a longitudinal axis of said cannula.

11. pen needle of claim 1, wherein said resilient first sleeve and said resilient second sleeve are compressible and foldable axially relative to said cannula when an axial force is applied to said resilient first sleeve and resilient second sleeve, respectively, and expandable to an original position to cover said cannula when said axial force is released.

12. The pen needle claim 1, wherein
said axial face of said distal post has a raised outer ring at an outer edge of said axial face, and a raised inner ring at a center portion of said axial face, said inner ring and said outer ring defining a skin shaping surface and defining a recess between said inner ring and said outer ring, and where said outer ring, said inner ring, and said recess define a convex surface having a continuous radius of curvature.

13. A pen needle comprising:
a needle hub having a side wall, a proximal open end, and an end wall at a distal closed end of said side wall, said proximal open end configured for coupling to a delivery device;
a distal post extending from said end wall of said needle hub and having an outer axial face, said outer axial face having an outer dimension less than an outer dimension of said side wall of said needle hub, said outer axial face of said distal post has a raised outer ring at an outer edge of said outer axial face, and a raised inner ring at a center portion of said outer axial face, said inner ring and said outer ring defining a skin shaping surface and defining a recess between said inner ring and said outer ring, and where said outer ring, said inner ring, and said recess define a convex surface having a continuous radius of curvature;

a proximal post extending from an inner surface of said end wall of said needle hub and extending toward said proximal open end of said needle hub;

a cannula having a first end extending from a distal end of said distal post for introducing a medication to a patient, and a second end extending from said proximal post for piercing a septum on the delivery device and positioned in a cavity defined by said side wall;

a resilient first sleeve having an end wall and an open end, said open end of said resilient first sleeve coupled to said distal post and enclosing said first end of said cannula, said resilient first sleeve being compressible and foldable onto said distal post when said cannula is inserted into the patient where said end wall of said resilient first sleeve conforms to said convex surface of said distal post; and a resilient second sleeve having an end wall and an open end, said open end of said resilient first sleeve coupled to said proximal post and enclosing said second end of said cannula, said resilient second sleeve being compressible and foldable onto said proximal post when said needle hub is connected to the delivery device.

14. The pen needle of claim 13, wherein said resilient first sleeve has a side wall with a proximal portion having a substantially cylindrical shaped side wall, said proximal portion of said side wall having an open proximal end with an inner dimension complementing an outer dimension of said distal post, and said end wall of said resilient first sleeve having a diameter greater than an outer diameter of a distal end portion of said side wall of said resilient first sleeve and having an opening extending through said end wall of said resilient first sleeve with a dimension to allow said cannula to pass through, and where said proximal end portion has a width greater than said distal end portion.

15. The pen needle of claim 14, wherein said resilient second sleeve has a substantially cylindrical side wall, said side wall of said resilient second sleeve having an open proximal end with an inner dimension complementing an outer dimension of said proximal post, and said end wall of said resilient second sleeve having a diameter greater than an outer diameter of said side wall of said resilient second sleeve and having an opening extending through said end wall of said resilient second sleeve with a dimension to allow said cannula to pass through.

16. The pen needle of claim 14, wherein said side wall of said resilient first sleeve has a conical shaped distal end proximate said end wall of said resilient first sleeve, and where said end wall of said resilient first sleeve has an axial face greater than an outer dimension of said conical shaped distal end of said side wall.

17. The pen needle of claim 13, where said outer axial face of said distal post has a radius of curvature of 6.0 mm to 9.0 mm.

* * * * *